(12) United States Patent
Purwanto

(10) Patent No.: US 8,033,994 B2
(45) Date of Patent: Oct. 11, 2011

(54) ENDOSCOPIC APPARATUS

(75) Inventor: Eko Purwanto, Saitama (JP)

(73) Assignee: Fujinon Corporation, Saitama (JP)

( * ) Notice: Subject to any disclaimer, the term of this patent is extended or adjusted under 35 U.S.C. 154(b) by 1245 days.

(21) Appl. No.: 11/715,917

(22) Filed: Mar. 9, 2007

(65) Prior Publication Data

US 2007/0213589 A1    Sep. 13, 2007

(30) Foreign Application Priority Data

Mar. 10, 2006    (JP) ................ P2006-066629

(51) Int. Cl.
*A61B 1/06* (2006.01)
(52) U.S. Cl. ..................................... 600/167
(58) Field of Classification Search .............. 600/129, 600/167–168
See application file for complete search history.

(56) References Cited

U.S. PATENT DOCUMENTS

| | | | | |
|---|---|---|---|---|
| 4,846,155 A * | 7/1989 | Kimura | .......................... | 600/109 |
| 5,490,015 A * | 2/1996 | Umeyama et al. | ............ | 359/824 |
| 5,876,327 A * | 3/1999 | Tsuyuki et al. | ................ | 600/112 |
| 6,067,421 A * | 5/2000 | Kitazawa et al. | ............. | 396/133 |
| 6,084,363 A * | 7/2000 | Mizumoto | .................... | 318/116 |
| 6,232,697 B1 * | 5/2001 | Mizumoto | .................... | 310/317 |
| 2001/0016680 A1* | 8/2001 | Minami et al. | ................ | 600/167 |
| 2004/0097791 A1* | 5/2004 | Tokuda et al. | ................ | 600/173 |
| 2004/0210108 A1* | 10/2004 | Shimizu et al. | ............... | 600/112 |
| 2005/0275315 A1* | 12/2005 | Manabe et al. | ............... | 310/328 |
| 2006/0062560 A1* | 3/2006 | Ito et al. | .......................... | 396/87 |
| 2006/0084841 A1* | 4/2006 | Minami | ........................ | 600/168 |

FOREIGN PATENT DOCUMENTS

| | | |
|---|---|---|
| DE | 19902413 C1 | 5/2000 |
| EP | 1-788-644 A2 | 5/2007 |
| JP | 4-52070 B2 | 8/1992 |
| JP | 11-316345 A | 11/1999 |
| JP | 2000-47118 A | 2/2000 |
| JP | 2002-051576 A | 2/2002 |
| JP | 3635525 B2 | 1/2005 |

OTHER PUBLICATIONS

JP Office Action issued on Mar. 8, 2011 in JP application No. 2006-066629.

* cited by examiner

*Primary Examiner* — Philip Smith
(74) *Attorney, Agent, or Firm* — Birch, Stewart, Kolasch & Birch, LLP

(57) ABSTRACT

An endoscopic apparatus comprises: a movable lens that is movably built in an objective optical system arranged at an tip of an insert part of an endoscope; a piezoelectric-element drive mechanism that causes the movable lens to move forward and backward in an optical axis direction due to driving of a piezoelectric element; a control circuit that provides a drive pulse to the piezoelectric element; and a storage section that stores respective ones of drive-pulse count data for moving the movable lens forward and backward equally in amount, wherein the control circuit performs control of providing a drive-pulse count, different in between forward and backward movement, to the piezoelectric element of the piezoelectric-element drive mechanism so as to move the movable lens forward and backward equally in amount depending upon drive-pulse count data read out of the storage section.

3 Claims, 4 Drawing Sheets

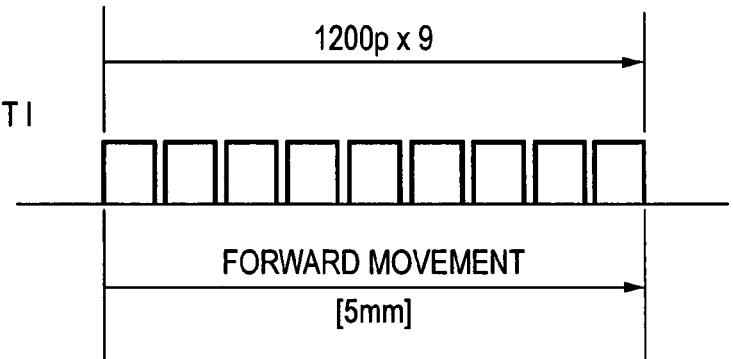
FIG. 4A FORWARD MOVEMENT I
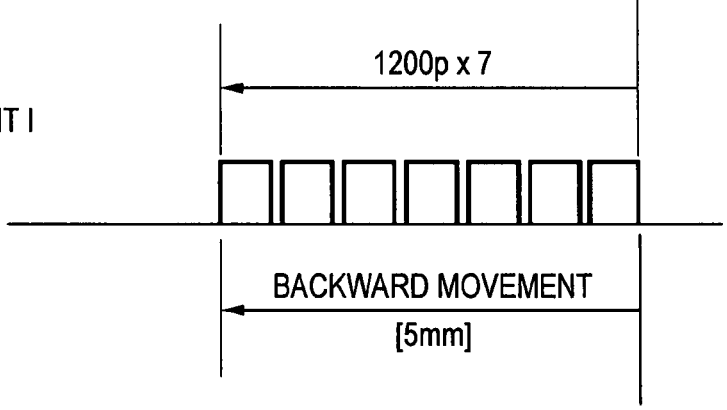
FIG. 4B BACKWARD MOVEMENT I
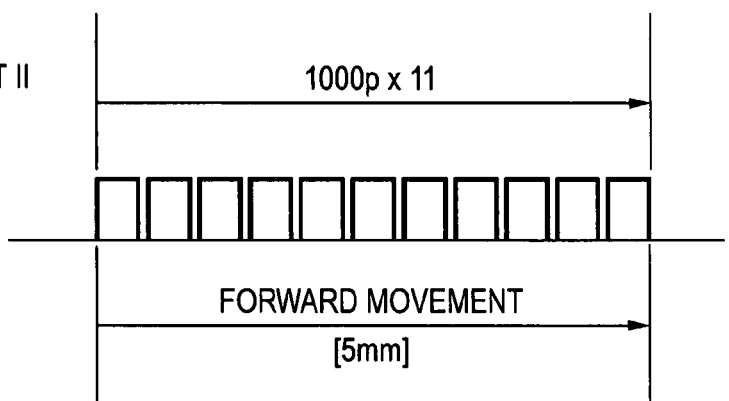
FIG. 4C FORWARD MOVEMENT II
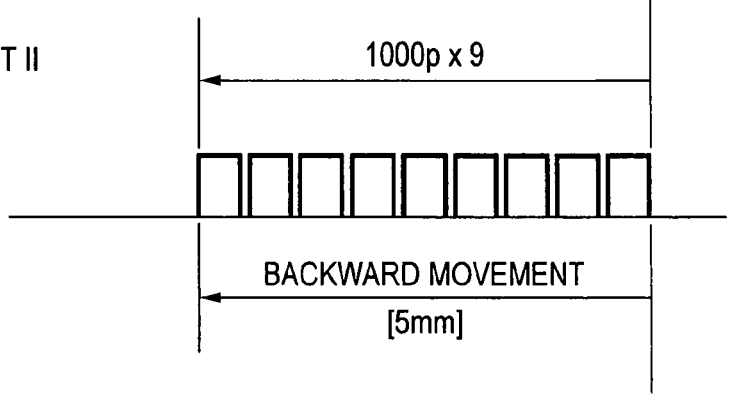
FIG. 4D BACKWARD MOVEMENT II

ENDOSCOPIC APPARATUS

BACKGROUND OF THE INVENTION

1. Field of the Invention

The present invention relates to endoscopic apparatuses and more particularly to piezoelectric-element drive mechanism control to drive the movable lens, arranged in an objective optical system, through expansion and contraction of a piezoelectric element for the purpose of auto-focusing and zooming functions.

2. Description of the Related Art

For example, the electronic endoscopic apparatus has an electronic endoscope (scope), a processor unit, a light source, a monitor and so on. In the tip of the electronic endoscope, there are arranged an objective optical system (lenses), a CCD (charge coupled device) serving as a solid-state imager, and so on. Depending upon the illumination of from the light source, the CCD takes an image of a subject-of-observation. The image signal is video-processed in the processor unit, to thereby display a video image of the subject-of-observation on the monitor. The objective optical system is built therein with a movable lens for the purpose of zooming and focusing functions. It is a recent practice to use a piezoelectric-element drive mechanism in order to drive such a movable lens.

In the piezoelectric-element drive mechanism, the drive shaft coupled to a piezoelectric element is frictionally engaged with a moving body so that the moving body can be moved slightly by delivering the expansion/contraction of the piezoelectric element to the moving body through the drive shaft (JP-B-4-52070 and Japanese Patent No. 3,635,525). By controlling the waveform, etc. of a drive voltage to be supplied to the piezoelectric element, the moving body can be moved in forward and backward directions. Such a piezoelectric-element drive mechanism is advantageously arranged in the tip of an endoscope having a reduced diameter because of its easiness to reduce the size.

However, in the movable lens movement control based on the conventional piezoelectric-element drive mechanism, when drive signals are provided in pulse count to drive the lens forward and backward equally in amount in the optical-axis direction, there encounters a difference of movement amount in between forward and backward movements thus resulting in a problem of the lowed accuracy of movement amount control. Namely, a difference occurs in moving amount in between the forward and backward due to the structure of the piezoelectric-element drive mechanism, such as a piezoelectric element as a drive source, a drive shaft coupled to the drive shaft, a frictional engagement state of between the drive shaft and the moving body. The difference depends also upon the characteristic unique to the piezoelectric-element drive mechanism, i.e. individual difference.

SUMMARY OF THE INVENTION

The present invention has been made in view of the foregoing problem, and it is an object thereof to provide an endoscopic apparatus that the forward and backward moving amount of the movable lens can be placed under control with accuracy due to a piezoelectric-element drive mechanism even where there is a difference in the movement amount of the movable lens in between the forward and backward or such a difference is based on an individual difference.

In order to achieve the foregoing object, the invention is an endoscopic apparatus comprising: a movable lens that is movably built in an objective optical system arranged at an tip of an insert part of an endoscope; a piezoelectric-element drive mechanism (a piezoelectric-element drive actuator) that causes the movable lens to move forward and backward in an optical axis direction due to driving of a piezoelectric element; a control circuit that provides a drive pulse to the piezoelectric element; and a storage section that stores respective ones of drive-pulse count data for moving the movable lens forward and backward equally in amount, wherein the control circuit performs control of providing a drive-pulse count, different in between forward and backward movement, to the piezoelectric element of the piezoelectric-element drive mechanism so as to move the movable lens forward and backward equally in amount depending upon drive-pulse count data read out of the storage section.

According to the above structure, the storage section in the emdoscopic apparatus is stored with drive-pulse count data for forward and backward movements each per unit amount (distance) [or predetermined amount (distance)], for example. When operating the piezoelectric-element drive mechanism, the drive-pulse count data is read out, based on which control is effected to move the movable lens a predetermined amount based on the pulse count different in between forward and backward movements. For example, to the piezoelectric element is supplied pulses in the number of 1200×9=(10800) as drive pulse count for a forward movement over a distance of 0.5 mm, and of 1200×7=(8400) as drive pulse count for a backward movement over the same distance. This makes it possible to move the movable lens forward and backward the same distance of 0.5 mm.

BRIEF DESCRIPTION OF THE DRAWINGS

FIGS. 4A to 4D are figures showing drive-pulse examples (I, II) of forward and backward movements formed in the example.

DETAILED DESCRIPTION OF THE INVENTION

Figure 1:
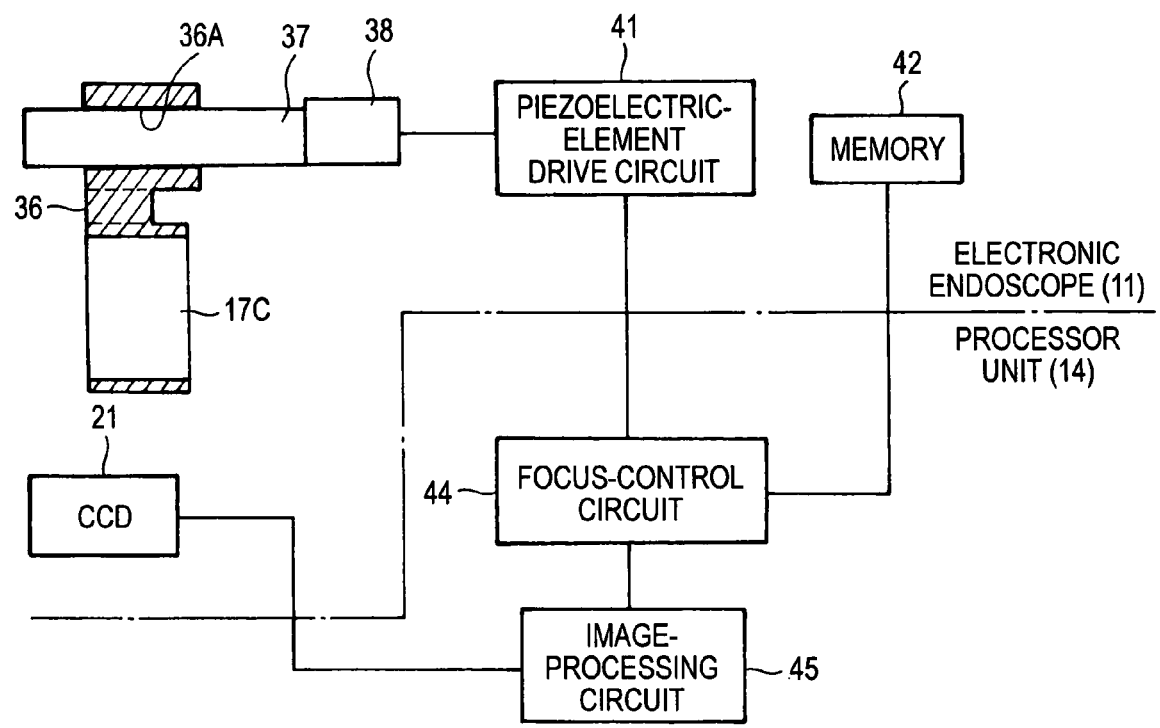
FIG. 1 is a diagram showing a main configuration of an electronic endoscopic apparatus according to an embodiment of the present invention.
Figure 2:
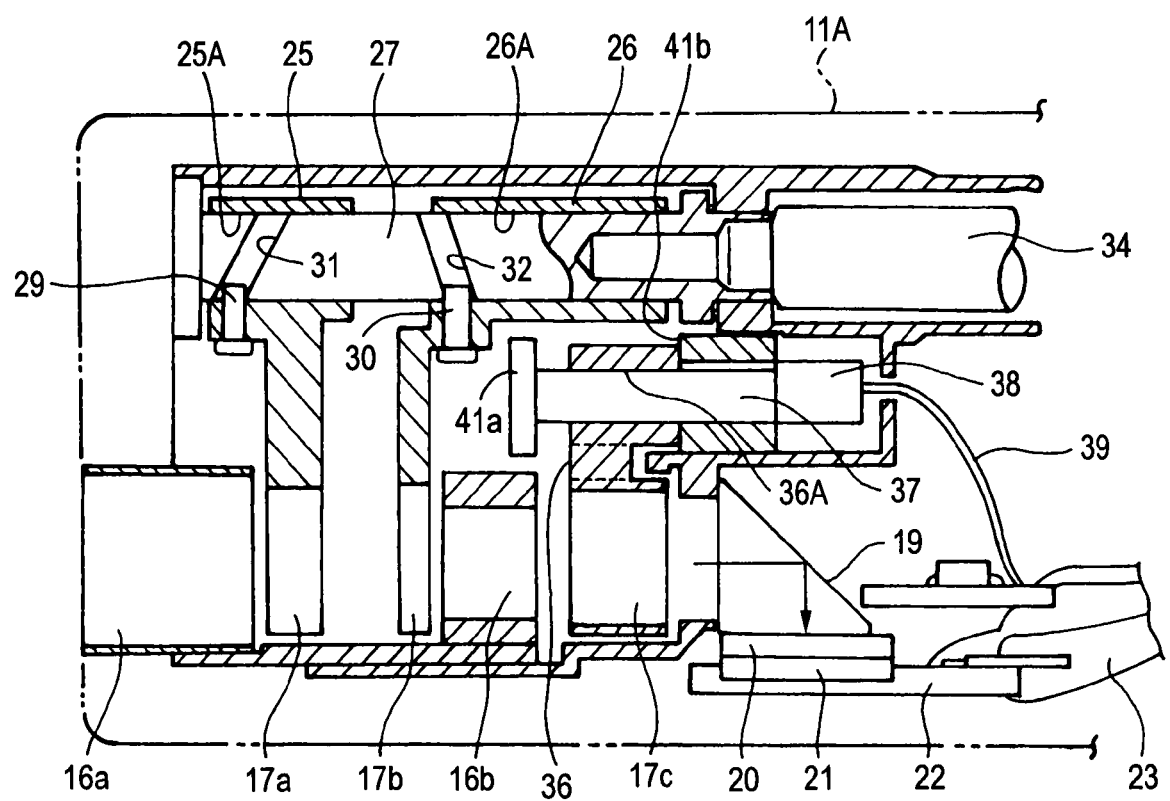
FIG. 2 is a sectional view showing an interior structure of an endoscopic tip portion in the embodiment.
Figure 3:
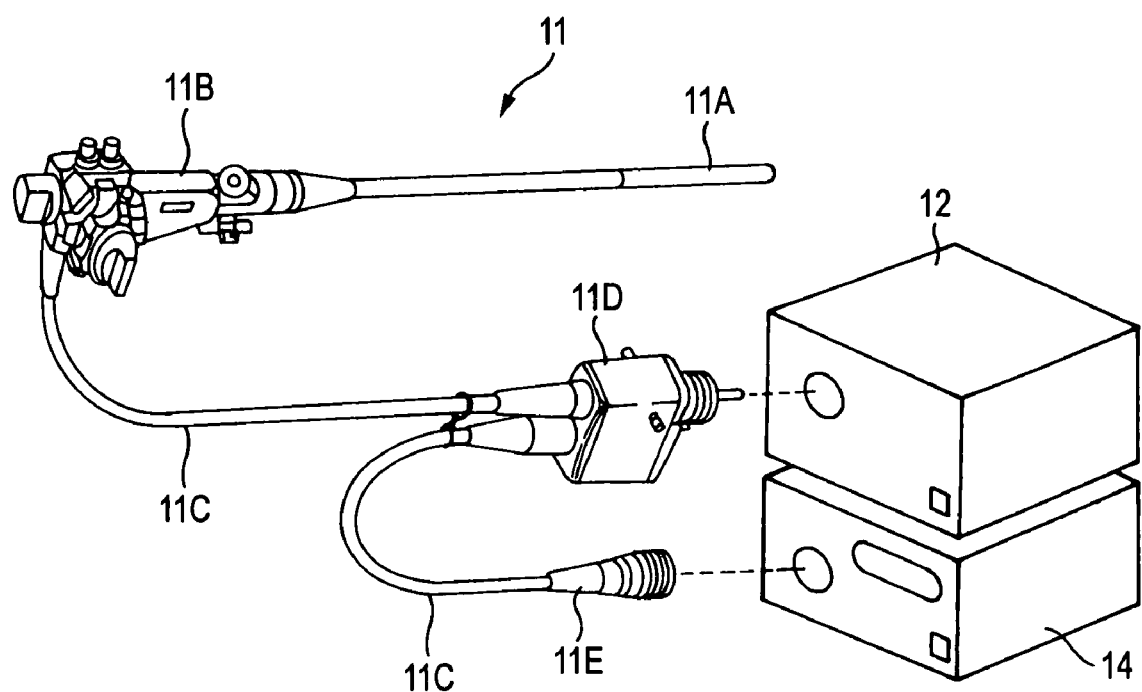
FIG. 3 is a view showing the overall exterior arrangement of the electronic endoscopic apparatus.

FIG. 1 shows a main arrangement of an electronic endoscopic apparatus according to an embodiment, FIG. 2 an interior construction of an endoscopic tip region, and FIG. 3 an exterior appearance of the electronic endoscopic apparatus. In FIG. 3, the electronic endoscopic apparatus includes an electronic endoscope (scope) 11 made up by an insertion part 11A as a portion to be inserted into a subject-of-observation and having an objective optical system at the tip and a solid-state imager, such as a CCD, an operation part 11B having an angular-operation knob, various switches, etc., a cable part 11C having a light-source connector 11D and an electric connector 11E, a light source 12 to which the electronic endoscope 11 is connected through the light-source connector 11D, a processor unit 14 to which the electronic endoscope 11 is connected through the electric connector 11E, and a not-shown monitor.

In FIG. 2, the insertion part 11A, at its tip, is arranged therein with an objective optical system that includes a fixed lens 16a including a viewing window, first and second movable lenses 17a, 17b for power change arranged as a variable-focal lens, a fixed lens 16b and a third movable lens 17c for focal adjustment, in the order closer to the front. In rear of the third movable lens 17c, there are arranged a prism 19 and, through a cover glass 20, a CCD 21 serving as a solid-state imager. The signal, taken at the CCD 21, is delivered to the processor unit 14 by way of a circuit board 22 and a signal line 23.

The first movable lens 17a is held by a support (holder frame) 25 having an engagement hole 25A while the second movable lens 17b is by a support 26 having an engagement hole 26A. In the state the engagement holes 25A, 26A fit over an outer periphery of a cylindrical camshaft 27, the lenses 17a, 17b are arranged on the camshaft 27. A cam pin 29 is arranged projecting for the engagement hole 25A while a cam pin 30 is for the engagement hole 26A. Meanwhile, in the camshaft 27, cam grooves 31, 32 are formed different in inclination direction with respect to the axis thereof so that the cam pin 29 engages in the cam groove 31 while the cam pin 30 in the cam groove 32.

The camshaft 27 is coupled with a linear-transmission member 34 formed by a multi-coiled spring or the like. The linear-transmission member 34 has the other end connected to a motor provided in the operation part 11B. Accordingly, by rotating the camshaft 27 due to motor driving through the linear-transmission member 34, the first and second movable lenses 17a, 17b are moved back and forth in the optical-axis direction through the engagement of the camshaft 31, 32 and the cam pin 29, 30. This causes a change of optical power. Namely, the first and second movable lenses 17a, 17b constitute a variable-focal optical system, to cause a change of optical power (made variable in observation distance, observation depth, focal length, etc.) while being moved back and forth.

Meanwhile, a small-sized piezoelectric-element drive mechanism (piezoelectric actuator) in order to drive the focusing, or third, movable lens 17c. The piezoelectric-element drive mechanism is arranged with a support (moving body) 36 serving as a holder frame sustaining the third movable lens 17c and formed with (cylindrical member having) an engagement hole 36A in the upper portion thereof, a cylindrical drive shaft (body) 37 frictionally engaged in the engagement hole 36A of the support 36, and a piezoelectric element 38 coupled (fixed) to the drive shaft 37. The piezoelectric element 38 is supplied with a drive pulse through the drive line 39. With the piezoelectric-element drive mechanism, by longitudinally moving the drive shaft 37 due to expansion/contraction driving of the piezoelectric element 38, the third movable lens 17c can be moved forward or backward.

Meanwhile, stoppers 41a, 41b are provided to bring the focusing, or third, movable lens 17c into stop at a start end (start point) and a termination end (termination point). In the embodiment, the start or termination point where the drive shaft 37 is restricted by the stopper 41a, 41b is detected by not-shown detecting means, such as a optical or magnetic sensor, e.g. photo-interrupter. This makes it possible to control the moving amount of the third movable lens 17c, from the start or termination point.

In FIG. 1, in addition to the CCD 21 arranged at the tip of the insertion part 11A, the endoscope 11 is arranged with a piezoelectric-element drive circuit 41 that provides a drive pulse for forward or backward movement to the piezoelectric element 38, and a memory (e.g. EEPROM) that stores drive-pulse count data (drive pulse count per unit amount or predetermined amount) for moving the third movable lens 17c forward and backward equally in amount. Namely, the drive pulse count per unit amount (unit distance) can be determined by operating [drive pulse count required for movement over the overall travel]÷[overall travel of the third movable lens 17c from its start end to termination end].

Meanwhile, the processor unit 14 is provided with a focus-control circuit 44 that places the piezoelectric-element drive circuit 41 under auto-focus control, and an image-processing circuit 45 that performs an image processing depending upon the output signal from the CCD 21 and outputting a signal representative of an image clarity for use in auto-focusing to the focus-control circuit 44.

The embodiment is structured as described so far. When the electronic endoscope 11 at its insertion part 11A is inserted in a subject-of-observation, the subject-of-observation is imaged by the CCD 21 through the objective optical system. Based upon the output signal from the CCD 21, a video image is formed in the image-processing circuit 45. Due to the video signal, a video image of the subject-of-observation is displayed on a monitor. Meanwhile, the image-processing circuit 45 extracts the signal representative of an image clarity and supplies the relevant signal to the focus-control circuit 44. From the signal representative of a clarity, the focus-control circuit 44 forms a control signal for focal adjustment, i.e. a signal regulating the forward or backward movement (distance) of the focusing, or third, movable lens 17c (i.e. moving direction-and-amount signal). The control signal is supplied to the piezoelectric-element drive circuit 41.

At this time, in the focus control circuit 44, there is read, out of the memory 42, the data of drive pulse count per unit or predetermined amount for forward or backward movement (drive pulse count for equal amount of movement). Depending upon the drive-pulse count data, a control signal of forward/backward-movement amount is supplied to the piezoelectric-element drive circuit 41. Incidentally, such drive-pulse count data may be inputted from the memory 42 directly to the piezoelectric-element drive circuit 41. The piezoelectric-element drive circuit 41 forms a drive pulse corresponding to the control signal of forward/backward-movement amount. The drive pulse is given as shown in FIGS. 4A and 4B.

FIGS. 4A and 4B show a drive pulse in a control example I. For a signal of forward movement amount of a distance of 5 mm, nine blocks are formed each including 1200 pulses (p) of signals at a frequency of 370 kHz (at a desired frequency), to thereby output drive pulses in the number of 1200×9=10800. For a signal of backward movement amount of the same distance 5 mm, seven blocks are formed each including 1200 pulses (p) of signals at a frequency of 370 kHz, to thereby output drive pulses in the number of 1200×7=8400. With such drive pulses, movement can be accurately effected over the same distance though movement rate is different due to the different number of drive pulses in between forward and backward directions.

FIGS. 4C and 4D show a drive pulse in a control example II wherein there is a difference in the number of one block from the control example I. This control example forms, as a signal of forward movement amount of a distance 5 mm, eleven blocks each including 1000 pulses (p) of signals at a frequency of 370 kHz, to output drive pulses in the number of 1000×11=11000. For a signal of backward movement amount of the same distance, nine blocks are formed each including 1000 pulses (p) of signals at a frequency of 370 kHz, to output drive pulses in the number of 1000×9=9000.

In this manner, in the piezoelectric-element drive mechanism of the electronic endoscope 11 of this embodiment, movements can be accurately effected forward and backward over the equal distance by means of the number of drive pulses. However, in the piezoelectric-element drive mechanism arranged in other electronic endoscope, drive pulses are formed and outputted in the number for forward and backward movements depending upon the drive-pulse count data for other electronic endoscope stored in the memory. Due to this, the movable lens for auto-focusing can be placed under movement control with accuracy even where there is an individual difference in the piezoelectric-element drive mechanism.

The embodiment explained the case of placing the focusing, or third, movable lens 17c under movement control. Besides, the piezoelectric-element drive mechanism in the invention may be arranged to drive first and second movable lenses 17a, 17b for variable power provided in the insertion part 11A.

According to the endoscopic apparatus of the invention, there is an effect that can place the forward and backward moving amount of the movable lens with accuracy due to a piezoelectric-element drive mechanism even where there is a difference in the movement amount of the movable lens in between forward and backward movements or such a difference is based on an individual difference.

The entire disclosure of each and every foreign patent application from which the benefit of foreign priority has been claimed in the present application is incorporated herein by reference, as if fully set forth.

What is claimed is:

1. An endoscopic apparatus comprising:
    a movable lens that is movably built in an objective optical system arranged at an tip of an insert part of an endoscope;
    a piezoelectric-element drive mechanism that causes the movable lens to move forward and backward in an optical axis direction due to driving of a piezoelectric element;
    a control circuit that provides a drive pulse to the piezoelectric element; and
    a storage section that stores a first drive-pulse count data for moving the movable lens forward by a predetermined amount and a second drive-pulse count data different from the first drive-pulse count data for moving the movable lens backward by an amount equal to the predetermined amount;
    wherein the control circuit provides the first drive-pulse count data to move the movable lens forward by the predetermined amount, and provides the second drive-pulse count data so as to move the movable lens backward by the amount equal to the predetermined amount.

2. The endoscopic apparatus according to claim 1, wherein the movable lens is for auto-focusing.

3. The endoscopic apparatus according to claim 1, wherein the movable lens is for variable power.

* * * * *